(12) United States Patent
Cunill Aixelà

(10) Patent No.: US 9,717,764 B2
(45) Date of Patent: Aug. 1, 2017

(54) EGG PREPARATION WITH REGENERATING, ANALGESIC AND/OR ANTI-INFLAMMATORY PROPERTIES

(75) Inventor: Juan Cunill Aixelà, Barcelona (ES)

(73) Assignee: OVIVITY GROUP, S.L., Barcelona (ES)

( * ) Notice: Subject to any disclaimer, the term of this patent is extended or adjusted under 35 U.S.C. 154(b) by 314 days.

(21) Appl. No.: 14/351,133

(22) PCT Filed: May 18, 2012

(86) PCT No.: PCT/EP2012/059251
§ 371 (c)(1),
(2), (4) Date: Apr. 10, 2014

(87) PCT Pub. No.: WO2013/053503
PCT Pub. Date: Apr. 18, 2013

(65) Prior Publication Data
US 2014/0255331 A1    Sep. 11, 2014

(30) Foreign Application Priority Data

Oct. 13, 2011 (EP) ..................................... 11184990

(51) Int. Cl.
| | |
|---|---|
| *A23L 15/00* | (2016.01) |
| *A23L 33/10* | (2016.01) |
| *A23K 20/00* | (2016.01) |
| *A61K 35/57* | (2015.01) |
| *A61Q 19/00* | (2006.01) |

(Continued)

(52) U.S. Cl.
CPC .............. *A61K 35/57* (2013.01); *A23K 20/00* (2016.05); *A23L 15/00* (2016.08); *A23L 33/10* (2016.08); *A61K 8/982* (2013.01); *A61Q 5/00* (2013.01); *A61Q 19/00* (2013.01)

(58) Field of Classification Search
None
See application file for complete search history.

(56) References Cited

FOREIGN PATENT DOCUMENTS

| CA | 2197050 A1 | 8/1998 |
|---|---|---|
| EP | 0904090 B1 | 1/2007 |

(Continued)

OTHER PUBLICATIONS

Jones, "Mound-Builders", 2008, pp. 1-119.*

(Continued)

*Primary Examiner* — Ernst V Arnold
*Assistant Examiner* — Kyung Sook Chang
(74) *Attorney, Agent, or Firm* — Peter B. Scull; Hamilton, DeSanctis & Cha LLP

(57) ABSTRACT

It comprises an egg preparation comprising a mixture of the yolk and the white extracted from a fertilized egg incubated for a period comprised between 18 hours and 36 hours, wherein the mixture of the yolk and white is in a ratio in which the amount of the white is comprised between 2% and 40% by volume of the yolk volume, useful as regenerating, analgesic and/or anti-inflammatory agent, as well as its preparation process. It also relates to functional foods, dietary supplements, and pharmaceutical or veterinary compositions containing the egg preparation. It also relates to cosmetic compositions comprising the egg preparation and to its use as skin care or hair or fur care agent.

19 Claims, 5 Drawing Sheets

(51) Int. Cl.
   A61Q 5/00      (2006.01)
   A61K 8/98      (2006.01)

(56)                References Cited

FOREIGN PATENT DOCUMENTS

| JP | 2002535279 A    | 10/2002 |
| WO | WO97/35595 A1   | 10/1997 |
| WO | WO00/43019 A2   |  7/2000 |
| WO | WO01/91777 A1   | 12/2001 |
| WO | WO2009/115429 A1|  9/2009 |

OTHER PUBLICATIONS

Science of Cooking, "The Anatomy of a Chicken Egg", pp. 1-2, published in 2009.*

Wayback machine sheet [(retrieved from on-line website https://web.archive.org/web/*/http://www.scienceofcooking.com/eggs/anatomy_chicken_egg.htm), access date: Jul. 8, 2016].*

Poultrykeeper Article, "Double or multi-yolk eggs," Dec. 1, 2009 [(retrieved from on-line website https://poultrykeeper.com/egg-problems/double-or-multi-yolk-eggs/, pp. 1-2, access date: Jul. 8, 2016)].*

Lisa M. Coussens et al. "Inflammation and cancer", Nature, vol. 420, pp. 860-867, Dec. 19/26, 2002, Nature Publishing Group, New York, NY.

Norman E Walker et al. "Distribution of chemicals injected into fertile eggs and its effect upon apparent toxicity", Toxicology and Applied Pharmacology, vol. 10, Issue 2, Mar. 1967, pp. 290-299, Elsevier, Inc., Philadelphia PA.

International Search Report and Written Opinion issued by the European Patent Office for International Application No. PCT/EP2012/059251, mail date Jun. 22, 2012, pp. 11, Rjawijk, Netherlands.

Whittow, G Causey, "Sturkie's Avian Physiology (Fifth Edition): Physiology of Growth and Development", Academic Press, Oct. 5, 1999, Chapter 25, pp. 635-656, Elsevier B.V., Amsterdam NL.

Mohammad Najmul Ghani Khan, Khazaain-al-Advia, vol. I, 5 (page No. 4-8) (Ref.pg. No. of publication:617 ), 1911 AD, Nadeem Yunus Printer / Sheikh Mohd Basheer & Sons, Lahore.†

Mohammad Akbar Arzani, Qaraabaadeen Qaadri, 4 (page No. 9-12) (Ref.pg. No. of publication:302 ), 1968 AD, Ahmadi Publication, Delhi, India.†

Mohammad Azam Khan, Ikseer Azam, vol. IV, 4 (page No. 13-16) (Ref.pg. No. of publication:309 ), 1872 AD, Matba Nizami, Kanpur, India.†

\* cited by examiner
† cited by third party

EGG PREPARATION WITH REGENERATING, ANALGESIC AND/OR ANTI-INFLAMMATORY PROPERTIES

The present invention relates to a preparation containing fertilized egg and its preparation process. It also relates to its therapeutic use as regenerating agent, analgesic agent and/or anti-inflammatory agent, and its cosmetic use. It also relates to the functional food, dietary supplement, pharmaceutical or veterinary composition containing the egg preparation of the invention.

BACKGROUND ART

Inflammation is part of the complex biological response of vascular tissues to harmful stimuli, such as pathogens, damaged cells, or irritants. Inflammation is a protective attempt by the organism to remove the injurious stimuli and to initiate the healing process.

It is characterized by fenestration of the microvasculature, leakage of the elements of blood into the interstitial spaces, and migrant of leukocytes into the inflamed tissue. On a macroscopic level, this is usually accompanied by the familiar clinical signs of erythem, edema, hyperalgesia, and pain.

Without inflammation, wounds and infections would never heal. Similarly, progressive destruction of the tissue would compromise the survival of the organism. However, chronic inflammation can also lead to a host of diseases, such as hay fever, atherosclerosis, rheumatoid arthritis, and even cancer (e.g., gallbladder carcinoma). It is for that reason that inflammation is normally closely regulated by the body.

L. Coussens et al. in "Inflammation and cancer", *Nature* 2002, vol. 420, pp. 860-867 describe that cancer is a condition related to inflammation. Recent data have expanded the concept that inflammation is a critical component of tumour progression. Many cancers arise from sites of infection, chronic irritation and inflammation. It is now becoming clear that the tumour microenvironment, which is largely orchestrated by inflammatory cells, is an indispensable participant in the neoplastic process, fostering proliferation, survival and migration.

In short, the inflammatory response causes much of the physical discomfort that has come to be associated with different diseases and injuries. It is known the administration of pharmacological agents that reduce the physical discomfort of the inflammatory response. Anti-inflammatory drugs are used for the treatment of a wide spectrum of disorders and the same drug is often used to treat different diseases. Treatment with anti-inflammatory drugs is not for the disease, but most often for the symptom.

Eggs, in particular hen's eggs, have been the subject of intensive chemical, biochemical and food technological research for many decades, because of its importance in human nutrition and it importance as a source of proteins. It is also known the use of egg products for the treatment of several disorders associated to inflammation.

EP0904090 describes an anti-inflammatory composition produced in natural foodstuff, particularly in egg products. The anti-inflammatory activity was found in a fraction isolated from both egg yolk and egg white of an egg.

CA2197050 describes an use of fertilized incubated shell eggs in the treatment and prevention of cancer.

WO0191777 describes a drug consisting of activated protein compounds obtained using a process involving heating, precipitation and purification of a mixture containing yolk and white of an egg, and pine resin rosin or pine needle oil, as well as its use in the treatment of tuberculosis, various cancers and other inflammatory diseases.

Finally, WO2009115429 describes a food preparation and pharmaceutical composition containing an embryonic extract and its uses in several disorders related to inflammation, in particular, it is described its use for the prevention of skin dryness, prevention of hair loss, stimulation of the defences indicated to combat infections or parasitic diseases in dogs and cats, treatment of cancer, as well as its use as regenerating agent, anti-degenerative agent or anti-inflammatory agent.

From what is known in the art, it is derived that the use of natural products such as egg preparations is of great interest in the field of medicine to treat disorders associated with inflammation. Thus, the provision of an improved egg preparation to treat several disorders related to inflammation would be still of great interest in the industry.

SUMMARY OF THE INVENTION

Inventors have found that an egg preparation comprising a mixture of yolk and white extracted from a fertilized egg which has been incubated for a short period, has analgesic and/or anti-inflammatory properties. It has also been found that it has regenerating properties. The preparation of the invention has resulted to be more efficacious than others egg preparations, and with respect to other known regenerating, analgesic and/or anti-inflammatory agents has the advantage of the natural origin of the preparation which implies that it is not toxic and does not produce side effects.

Nothing in the art suggests that an egg preparation with a mixture of yolk and white in a specific ratio from an egg incubated for a period comprised between 18 and 36 hours could confer to the preparation the excellent regenerating, analgesic and anti-inflammatory properties found in the egg preparation of the invention.

In addition, the inventors have found that the egg preparation of the invention is also useful as skin care and hair or fur care agent.

Accordingly, a first aspect of the present invention relates to an egg preparation comprising a mixture of the yolk and the white extracted from a fertilized egg incubated for a period comprised between 18 hours and 36 hours, wherein the mixture of the yolk and white is in a ratio in which the amount of the white is comprised between 2% and 40% by volume of the yolk volume.

A second aspect of the invention relates to a process for preparing the egg preparation as defined above which comprises: (a) Incubating a fertilized egg for a period comprised between 18 hours and 36 hours; (b) Collecting an amount of the yolk and an amount of the white of the incubated fertilized egg obtained in the previous step, and mixing the yolk and the white in a ratio in which the amount of the white is comprised between 2% and 40% by volume of the yolk volume; (c) Homogenizing the mixture of yolk and white obtained in step b); and (d) Quenching the egg preparation obtained in step c).

It is possible to use the preparation of the invention as part of a nutritional composition food. This said functional food has a positive effect on the person's health. Thus, a third aspect of the present invention refers to a functional food comprising the egg preparation of the invention. Also it is possible to use the preparation of the invention as part of a dietary supplement. Thus, a fourth aspect of the present invention refers to a dietary supplement comprising the egg preparation of the invention.

A fifth aspect of the invention refers to a pharmaceutical composition comprising an egg preparation as defined above, together with pharmaceutical excipients or carriers. Preferably, the pharmaceutical composition comprises an effective amount of an egg preparation as defined above, together with one or more pharmaceutical excipients or carriers.

A sixth aspect of the invention refers to a veterinary composition comprising an egg preparation as defined above, together with veterinary excipients or carriers. Preferably, the veterinary composition comprises an effective amount of an egg preparation as defined above, together with one or more veterinary excipients or carriers.

A seventh aspect of the invention refers to a cosmetic composition comprising an effective amount of an egg preparation as defined above, together with one or more cosmetic excipients or carriers.

The fact that the preparation of the present invention shows excellent analgesic properties is advantageous for its use for the treatment of acute or chronic pain in conditions related to pain. Consequently, an eight aspect of the present invention relates to the preparation as defined above, for use as analgesic agent for the treatment of acute or chronic pain in conditions related to pain.

The fact that the preparation of the present invention shows excellent regenerating properties allows its use as tissue regenerative agents. Egg yolk and egg white comprise proteins. Among them are growth factors. The growth factors control the embryonic growth. Numerous growth factors have been described, for example IGF (Insulin growth factor), FGF (fibroblast growth factor), NFG (nerve growth factor), EGF (epidermal growth factor) among others. The expression pattern of the different growth factors in the different development stages varies and it varies in yolk and white. The inventors have achieved the extraction of the growth factors having cell proliferative activity at the point where their activity is maximum. Thus, this fact contributes to the excellent regenerating properties of the preparation of the invention.

Apoptosis has been implicated in degenerative diseases. The sample of the invention inhibited the apoptosis. Therefore, this inhibition activity provides anti-degenerative properties. Therefore, a ninth aspect of the present invention relates to the preparation as defined above, for use as regenerating agent for the treatment of degenerative conditions.

Further, the fact that the preparation of the present invention shows excellent anti-inflammatory properties is advantageous for its use as anti-inflammatory agent for the treatment of inflammatory conditions. Therefore, a tenth aspect of the present invention relates to the egg preparation as defined above, for use as anti-inflammatory agent for the treatment of inflammatory conditions.

Finally, since the egg preparation of the invention is also useful for the care of skin and hair or fur, an eleventh aspect of the invention refers to the cosmetic use of an egg preparation as defined above as a skin care agent; and a twelfth aspect of the invention refers to the cosmetic use of an egg preparation as defined above as a hair or fur care agent.

BRIEF DESCRIPTION OF THE DRAWINGS

FIG. 7 shows the results of an Experimental Autoimmune Encephalitis (EAE) animal model (Group D: animals without treatment; Group E: treatment with non fertilized egg (6); and Group F: (treatment with egg preparation of the invention, yolk extract (2)).

FIG. 8 shows the results of neuronal regeneration in an axotomy model. The animals tested were divided into the following groups: control animals not subjected to axotomy: Group A (without treatment), Group B (treatment with non fertilized egg (6)), and Group C (treatment with yolk extract (2)), and axotomized animals: Group D (treatment with non fertilized egg (6)), and Group E (treatment with yolk extract (2)).

DETAILED DESCRIPTION OF THE INVENTION

Figure 1:
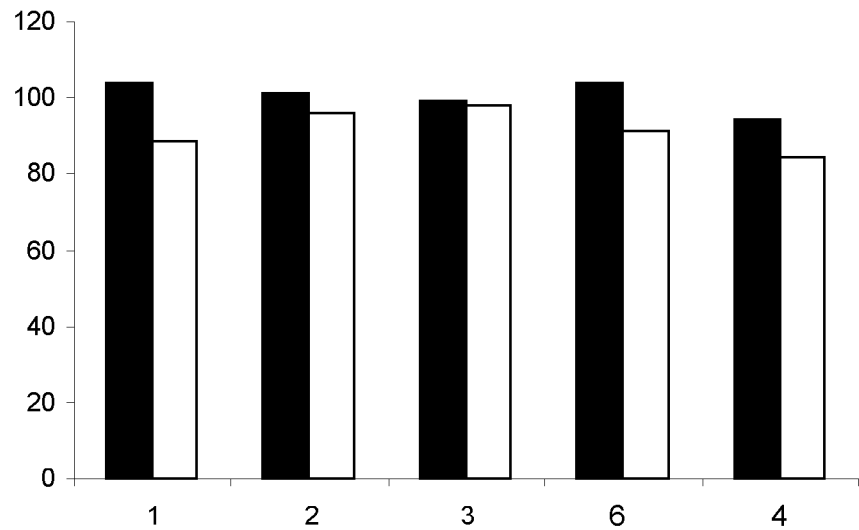
FIG. 1 shows the cell viability percentage in HMEC for different comparative samples, embryonic extract (1), not incubated egg (3), non fertilized egg (6), and enzymatic control (4), as well as for the sample according to the invention, yolk extract (2). The samples were diluted at 0.5% (white column) and at 1% (black column).

As mentioned above, an aspect of the present invention relates to an egg preparation comprising a mixture of the yolk and the white extracted from a fertilized egg incubated for a period comprised between 18 hours and 36 hours, wherein the mixture of the yolk and white is in a ratio in which the amount of the white is comprised between 2% and 40% by volume of the yolk volume. In a preferred embodiment, the egg preparations consists of a mixture of the yolk and the white extracted from a fertilized egg incubated for a period comprised between 18 hours and 36 hours, wherein the mixture of the yolk and white is in a ratio in which the amount of the white is comprised between 2% and 40% by volume of the yolk volume.

The preparation of the invention is more active, when the white is in a percentage equal or higher than 5%. Therefore, in a preferred embodiment, the amount of white is comprised between 5% and 40% by volume of the yolk volume. In another preferred embodiment, the amount of white is comprised between 5% and 30% by volume of the yolk volume. In another more preferred embodiment, the amount of white is comprised between 7% and 15% by volume of the yolk volume. In still another more preferred embodiment the amount of white is 10% by volume of the yolk volume.

There are two types of white in the egg, fluid and dense. In particular, the egg white is composed by several parts: an external part containing fluid white (named herein as external fluid white); an internal part containing fluid white (named herein as internal fluid white), which is attached to the yolk by surrounding it; and a dense white part (named herein as dense white), which is placed between the two fluid white parts.

In a preferred embodiment the white in the egg preparation of the invention is fluid white. In a more preferred embodiment, the white in the egg preparation of the invention is the internal fluid white.

The inventors have found that the internal fluid white is about 40% by volume of the yolk volume. If the egg preparation comprises a higher % of the white, so that the egg preparation contains internal fluid white and also external fluid white and/or dense white, the egg preparation becomes more diluted because the additional white does not have the advantageous properties of the internal fluid white, but the egg preparation still maintains their therapeutic and cosmetic properties. Thus, in a particular embodiment, the egg preparation of the invention further comprises external fluid white and/or dense white, in an amount such that the sum of internal fluid white, external fluid white, and dense white in the egg preparation is up to 99% by volume of the sum of yolk and total white volumes.

The term "incubated" as used herein, refers to maintain constant the incubation temperature of the egg. In a preferred embodiment, the incubation temperature is comprised between 34° C. and 41° C. In a more preferred embodiment the incubation temperature is comprised between 35.5-37° C. In a still more preferred embodiment, the incubation temperature is comprised between 35.5-36.8° C. These temperature specific conditions make not possible the chicken embryo development. In a particular embodiment, the temperature is selected from the following temperatures, 34° C., 35° C., 36° C., 37° C., 38° C., 39° C., 40° C., 41° C.

As mentioned above, the incubation period is comprised between 18 hours and 36 hours, this period comprising the gastrula stage.

The term "gastrula stage" as used herein, refers to an early phase in the embryonic development of the avian, during which the single layered blastula is reorganized into a trilaminar structure known as the gastrula. These three germ layers are known as the ectoderm, mesoderm, and endoderm. Chick gastrulation is finished following 24 hours to 28 hours of incubation.

Eggs incubated for such period between 18 hours to 36 hours in a pre-gastrula phase, gastrula phase and post gastrula phase show the expression pattern of the different growth factors in the optimal concentrations to use the preparation of the invention for use as regenerative, anti-inflammatory and analgesic agent.

In a preferred embodiment, the eggs used are avian eggs. In a more preferred embodiment the eggs used are birds bred for egg production, for example hens, geese, ducks, quail, turkeys, ostriches, pheasants, pigeons. In a particular embodiment, the eggs are hen eggs.

The egg preparation of the invention is prepared by a process which comprises: (a) Incubating a fertilized egg for a period comprised between 18 hours and 36 hours; (b) Collecting an amount of the yolk and an amount of the white of the incubated fertilized egg obtained in the previous step, and mixing the yolk and the white in a ratio in which the amount of the white is comprised between 2% and 40% by volume of the yolk volume; (c) Homogenizing the mixture of yolk and white obtained in step b); and (d) Quenching the egg preparation obtained in step c).

In a preferred embodiment, the period is comprised between 20 and 28 hours. In another preferred embodiment, the period is comprised between 22 and 26 hours. In a more preferred embodiment, the period is 24 hours.

In another preferred embodiment, step a) is carried out at a temperature selected from the following temperatures, 34° C., 35° C., 36° C., 37° C., 38° C., 39° C., 40° C., 41° C., for a period comprised between 22 and 26 hours.

The proteins in the egg preparation for example growth factors are unstable, the protein denaturation can occur with high temperature among other physical features. Thus, in a preferred embodiment the process further comprises an additional step of refrigerating the incubated egg obtained in step a).

The quenching step (d) is carried out to stop the process and preserve the properties of the egg preparation obtained in step c). The quenching step comprises decreasing the temperature below 34° C., more preferably below 0° C., more preferably at about −18° C. In a preferred embodiment, the quenching step is a freezing step. In another preferred embodiment, the quenching step is a freeze drying step.

Optionally, when the egg preparation further comprises external fluid white and/or dense white, the process further comprises the step of mixing the specific amount of external fluid white and/or dense white.

The egg preparation of the present invention can also be defined as an egg preparation obtainable by the process defined above. Thus, it also forms part of the invention an egg preparation comprising a mixture of yolk and white in a ratio in which the amount of the white is comprised between 2% and 40% by volume of the yolk volume, obtainable by a preparation process comprising the following steps: (a) Incubating a fertilized egg for a period comprised between 18 hours and 36 hours; (b) Collecting an amount of the yolk and an amount of the white of the incubated fertilized egg obtained in the previous step, and mixing the yolk and the white in a ratio in which the amount of the white is comprised between 2% and 40% by volume of the yolk volume; (c) Homogenizing the mixture of yolk and white obtained in step b); and (d) Quenching the egg preparation obtained in step c). Preferred embodiments are egg preparations obtainable by any of the preferred embodiments of the process defined above.

The egg preparation "obtainable by" the process of the invention as defined above is used here to define the egg preparation by the process for obtaining it and refers to the egg preparation obtainable by the preparation process comprising the steps a), b), c), and d) as defined above. For the purposes of the invention the expressions "obtainable", "obtained" and equivalent expressions are used interchangeably, and in any case, the expression "obtainable" encompasses the expression "obtained".

A functional food or dietary supplement comprising the egg preparation of the invention, as well as pharmaceutical or veterinary compositions comprising the egg preparation as defined above also form part of the invention.

The term "functional food" as used herein, refers to a food where the egg product of the present invention has been added. In general, functional foods are part of the continuum of products that individuals may consume to increase their health and/or contribute to reducing their disease burden.

The term "dietary supplement" as used herein, refers to a preparation intended to supplement the diet and provide nutrients, such as vitamins, minerals, fiber, fatty acids or aminoacids, that may be missing or may not be consumed in sufficient quantities in a person's diet. The term dietary supplement intends to include the terms generally used in the field, for instance, nutraceutical or enriched supplement.

It is possible the administration of the preparation of the invention without any additives, excipients or carriers.

Alternatively, the egg preparation of the invention may comprise additional compounds, for example additives. Examples of additives include antioxidants such as vitamin C, flavours such as glutamic acid, preservatives such as rosemary extract, or stabilizers such as agar or pectin.

In a preferred embodiment, the egg preparation of the invention is administered to mammals, including humans.

The egg preparation of the invention may be an oral dosage form. In a preferred embodiment, the oral dosage form is a liquid. In a preferred embodiment, the administration of the egg preparation is sublingual administration.

In another preferred embodiment, the egg preparation of the invention is a solid dry form, particularly a powder form. The egg preparation in a powder form may be a freeze dried form. A freeze dried preparation can be easily mixed with others compounds, for example additives and has a shelf life which facilitates its manufacture, packaging, transport and storage.

In a preferred embodiment, the preparation of the present invention is loaded into capsules or pearls.

In another preferred embodiment, the preparation of the present invention is loaded into micelles.

The egg preparation of the invention may also be applied by topical administration. The topical compositions of the invention can be formulated in several forms that include, but are not limited to, solutions, aerosols and non-aerosol sprays, facial masks, shaving creams, powders, mousses, lotions, gels, sticks, ointments, pastes, creams, shampoos, rinse creams, hair conditioners, shower gel, body washes or face washes. Generally, the topical compositions may comprise from 1% to 15% by volume of the egg preparation of the invention with respect to the total volume of the composition.

The topical compositions of the invention can be prepared according to methods well known in the state of the art. The appropriate excipients and/or carriers, and their amounts, can readily be determined by those skilled in the art according to the type of formulation being prepared.

As mentioned above, the present invention relates to pharmaceutical compositions, veterinary compositions and cosmetic compositions comprising an effective amount of an egg preparation as defined above, together with one or more pharmaceutical, veterinary or cosmetic excipients or carriers.

For the purposes of the present invention, the term "effective amount" means an amount that is sufficient to obtain the expected effect. In the case of the pharmaceutical and veterinary compositions the effective amount is the "therapeutically effective amount" and refers to the amount of a compound that, when administered, is sufficient to prevent development of, alleviate to some extent, one or more of the symptoms of the disorder, disease, or condition being treated. The particular dose of compound administered according to this invention will of course be determined by the particular circumstances surrounding the case, including the compound administered, the route of administration, the particular condition being treated, and the similar considerations.

The expression "pharmaceutically or veterinary acceptable excipients or carriers" refers to pharmaceutically or veterinary acceptable materials, compositions or vehicles for use in the pharmaceutical or veterinary technology for preparing compositions with medical use. Each component must be pharmaceutically or veterinary acceptable in the sense of being compatible with the other ingredients of the pharmaceutical or the veterinarian composition. It must also be suitable for use in contact with the tissue or organ of humans or animals without excessive toxicity, irritation, allergic response, immunogenicity or other problems or complications commensurate with a reasonable benefit/risk ratio.

The expression "cosmetically acceptable excipients or carriers" refers to that excipients or carriers suitable for use in contact with animal or human skin without undue toxicity, incompatibility, instability, allergic response, among others.

The pharmaceutical and veterinary compositions are preferably for oral administration, and may be presented as a liquid, powders, tablets, coated tablets or capsules. In a preferred embodiment, the pharmaceutical, veterinary, and cosmetic compositions are for oral administration, and may be presented as a liquid, powders, tablets, coated tablets, capsules or pearls. In another preferred embodiment, the pharmaceutical, veterinary, and cosmetic compositions are for topical administration.

As mentioned above, it is part of the invention the egg preparation for use in the treatment of acute or chronic pain in conditions related to pain, i.e. for use as analgesic agent. This aspect of the invention can also be formulated as use of the egg preparation of the present invention for the preparation of a medicament for the treatment of acute or chronic pain in conditions related to pain. The invention also relates to a method of treatment of a mammal, including a human, suffering from acute or chronic pain, said method comprising the administration to said mammal, including a human, of a therapeutically effective amount of the egg preparation of the present invention, together with acceptable excipients or carriers.

Preferably, the treatment is a coadyuvant treatment. Thus, the egg preparation of the invention can be administered in combination with other known analgesic agents.

In a preferred embodiment, the dose of the egg preparation is selected from 5-30 mL. In another preferred embodiment, the dose is selected from 5-15 mL. In a particular embodiment the dose is selected from the following: 5 mL, 10 mL, 15 mL, 20 mL, 25 mL, and 30 mL of the egg preparation.

Generally, the daily dose for a mammal of the egg preparation used for therapeutic purposes in the pharmaceutical or veterinary field is from 3-48 mL, which can be administered together with pharmaceutically or veterinary acceptable excipients or carriers as mentioned above. In a more preferred embodiment, the daily dose is 5-30 mL. In an even more preferred embodiment, the daily dose is 5-15 mL. In a particular embodiment, the daily dose is selected from the following: 3 mL, 5 mL, 6 mL, 9 mL, 10 mL, 12 mL, 15 mL, 18 mL, 20 mL, 21 mL, 24 mL, 25 mL, 27 mL, 30 mL, 36 mL, 42 mL, and 48 mL of the egg preparation. The specific dose to be administered will depend on several factors, such as the type of mammal, including a human, its weight, as well as the severity of the symptoms.

As mentioned above, the egg preparation of the invention can be administered to mammals, including humans, without any additives, excipients or carriers, or in the form of a pharmaceutical, veterinary or cosmetic composition. In general, the dose used for cosmetic purposes is lower than the dosage used for therapeutic purposes.

The term "analgesic agent" as used herein, refers to an agent with the aim of alleviating the acute or chronic pain. The chronic pain means that a pain continuing for six months, which appears after a recovery of a tissue damage resulting in acute pain.

In a preferred embodiment, the condition related to pain is selected from arthritis, arthrosis, and backache. In another preferred embodiment, the condition related to pain is chronic fatigue syndrome. In a more preferred embodiment, the condition related to pain is fibromyalgia.

It is also part of the invention the egg preparation for use in the treatment of degenerative conditions. i.e. for use as anti-degenerative agent. This aspect of the invention can also be formulated as use of the egg preparation of the present invention for the preparation of a medicament for the treatment of degenerative conditions. The invention also relates to a method of treatment of a mammal, including a human, suffering from a degenerative condition, said method comprising the administration to said mammal, including a human of a therapeutically effective amount of the egg preparation of the present invention, together with acceptable excipients or carriers.

Preferably, the treatment is a coadyuvant treatment. Thus, the egg preparation of the invention can be administered in combination with other known regenerating agents.

The term "regeneration agent" as used herein, refers to an agent for promoting tissue formation or regeneration.

In a preferred embodiment, the degenerative condition is skin aging. In a more preferred embodiment, the condition is psoriasis. In another preferred embodiment, the condition is multiple sclerosis. In another preferred embodiment, the condition is spinal disc hernia. In another preferred embodiment, the condition is rheumatoid arthritis. In another preferred embodiment, the condition is Friedreich ataxia. In another preferred embodiment, the condition is a neurodegenerative disease. Examples of such neurodegenerative disease include Parkinson's disease, Huntington's disease, Alzheimer's disease, senile dementia, and Amyloid Lateral Schlerosis (ALS).

In another embodiment, the egg preparation of the invention is used in the treatment of scars, burns and abrasions.

As mentioned above, it is part of the invention the egg preparation for use in the treatment of inflammatory conditions, i.e. for use as anti-inflammatory agent. This aspect of the invention can also be formulated as use of the egg preparation of the present invention for the preparation of a medicament for the treatment of conditions related to inflammation. The invention also relates to a method of treatment of a mammal, including a human, suffering from inflammatory condition, said method comprising the administration to said mammal, including a human of a therapeutically effective amount of the egg preparation of the present invention, together with acceptable excipients or carriers.

Preferably, the treatment is a coadyuvant treatment. Thus, the egg preparation of the invention can be administered in combination with other known anti-inflammatory agents.

The term "anti-inflammatory" as used herein, refers to an agent with the aim of reducing inflammation.

In a preferred embodiment the inflammatory condition is cancer. In another preferred embodiment, the condition is chronic obstructive pulmonary disease. In another preferred embodiment, the condition is multiple sclerosis.

For the purposes of the present disclosure, the term "treatment" means compensation for a physiological dysfunction and more generally reduction or even elimination of an undesirable disorder, the manifestation of which is especially a consequence of this dysfunction.

In another preferred embodiment, the egg preparation of the invention is administered to cats, dogs and horses. In the case of dogs, efficacy has been shown in the treatment of musculoskeletal disorders such as contusions, arthritis, or arthrosis by an improvement of the inflammation, pain, and mobility; as well as nervous system diseases such inflammatory diseases (e.g., meningitis caused by virus or herniated disc with spinal cord affection) by improving the inflammation, the nerve regeneration and functionality. In cats, efficacy has been particularly shown in animals suffering from immunosuppression.

In the case of horses, efficacy has been shown in the treatment of acute or chronic lameness and mobility problems caused by age-related or acquired degenerative diseases, such as arthritis, loss of elasticity and calcifications of tendons. It has also shown efficacy in the treatment of acute or chronic lameness or other disorders due to problems in muscles, tendons, bones, cartilages or joint related structures; in the treatment of acute or chronic lameness due to equine hoof disorders or disorders other than joint problems. It can also be used in recovery periods such as recovery from surgery and recovery from immobilization, as coadyuvant treatment in combination with analgesics and/or anti-inflammatory drugs, and as coadyuvant treatment in cases of malnutrition and poor racing and competing performance. The egg preparation of the invention can also be used for improving the performance and recovery after equine competitions or situations involving a high energy or metabolic expenditure. It could also be useful in the treatment of neurodegenerative diseases, vascular disease, iatrogenic diseases, traumatic diseases, congenital disorders, metabolic diseases, immunologic disorders, and idiopathic diseases.

As mentioned above, the egg preparation of the invention can also be used for cosmetic purposes. Thus, the present invention also relates to a cosmetic use of the egg preparation as defined above as a skin care agent. The skin care may comprise ameliorating at least one of the following symptoms: roughness, flakiness, dehydration, tightness, chapping, and lack of elasticity. It also forms part of the invention a cosmetic method for skin care of a mammal, including a human, said method comprising the administration to said mammal, including a human, of an effective amount of the egg preparation as defined above, together with acceptable excipients or carriers. In particular the mammal, including a human may suffer or is susceptible to suffer from at least one of the following symptoms: roughness, flakiness, dehydration, tightness, chapping, and lack of elasticity.

Further, the present invention also relates to a cosmetic use of an egg preparation as defined above as a hair or fur care agent. The hair or fur care may comprise ameliorating the hair or fur structure and/or the physical-optical hair or fur properties. Examples of physical-optical hair or fur properties include: shine, dryness, smoothness and flexibility. In a preferred embodiment, the hair or fur care comprises preventing hair or fur loss and/or promoting hair or fur growth. It also forms part of the invention a cosmetic method for hair or fur care of a mammal, including a human, said method comprising the administration to said mammal, including a human, of an effective amount of the egg preparation as defined above, together with acceptable excipients or carriers. In particular, the hair or fur care comprises ameliorating the hair or fur structure and/or the physical-optical hair or fur properties, preventing hair or fur loss and/or promoting hair or fur growth.

The term "cosmetic" is intended to denote a use intended, principally, to provide an aesthetic and/or comfort effect, in particular, to ameliorate the appearance of the skin, specifically the properties of the skin.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

The incubated samples as described in the examples below were obtained by incubating a fertilized hen egg at a temperature of 36.8° C. for 24 h, sucking and homogenizing the specified amount of yolk and white, and freezing the mixture at −18° C.

Example 1

Acute Oral Toxicity Assays

Comparative sample 1, embryonic extract (1). A fertilized hen egg was removed from the incubator after 24 hours. The content obtained after the breaking of the shell, formed by the yolk and the white was deposited on a sterile tray. The yolk was shaken by rocking the tray until the embryonic germ was located in a dorsal and centered position. In said position, the suction of said embryonic germ was then carried out. Some amount of yolk or white could have been sucked.

Sample 2, yolk extract (2). A fertilized hen egg was removed from the incubator after 24 hours. The content obtained after the breaking of the shell, formed by the yolk and the white was deposited on a sterile tray; 5.5 mL of yolk and 0.5 mL of white were sucked.

Comparative sample 3, not incubated egg (3). A fertilized hen egg not incubated was broken and the yolk and the white were deposited on a sterile tray; 5.5 mL of yolk and 0.5 mL of white were sucked.

Comparative sample 4, enzymatic control (4): pepsin and lipase.

Comparative sample 5, medium control (5): culture medium.

Comparative sample 6, non fertilized egg (6): A non fertilized hen egg was broken and the yolk and the white were deposited on a sterile tray; 5.5 mL of yolk and 0.5 mL of white were sucked.

Comparative sample 7, water control (7): 6.0 mL of water.

These samples were used in the in vivo and in the in vitro toxicity assays. The controls used in vitro and in vivo assays are described below.

In Vitro Acute Toxicity Assay. Cell Viability Assay

An enzymatic digestion (pepsin 200 mg/mL 37° C., pH 1.5, 1 hour and lipase 14 mg/ml, 37° C., pH 7.5, 1.5 hours) of the samples (comparative embryonic extract (1), yolk extract (2), comparative not incubated egg (3), comparative non fertilized egg (6), and comparative enzymatic control (4)) was carried out. The samples were filtrated (0.45 µm) and diluted to concentrations of 0.5% and 1.0% by volume in the culture medium.

The cell viability of HMEC (Human Microvascular Endothelial Cells) was evaluated by the crystal violet method. In this assay, the dye stains the DNA of the cells. The amount of dye is proportional to the number of live cells in the culture.

FIG. 1 shows the results. There are not any significant differences in the cellular viability between the egg preparation of the invention (sample (2)) and the comparative samples, including the enzymatic control.

In Vivo Acute Oral Toxicity Assay

Sprague Dawley male and female rats in a ratio 6/4 were used. The rats were 4 weeks old. The animals were housed individually. For feeding conventional rodent laboratory diet (Harlan 2014) was used with an unlimited supply of drinking water. The samples (comparative embryonic extract (1), yolk extract (2), comparative not incubated egg (3), comparative non fertilized egg (6), and comparative water control (7)) were administered by gavage by orogastric tube. All animals were followed up to 14 days for assessment of mortality rate.

The animals were dosed, one at time, in a single ordered dose progression (5 mg/kg, 50 mg/kg, 300 mg/kg, and 2000 mg/kg), at a minimum of 48 hours intervals. The first animal received a dose of 5 mg/kg. As the animal survives, the dose for the second animal was 50 mg/kg. As the animal survives the dose for the third animal was 300 mg/kg. Finally, the dose for the fourth animal was 2000 mg/kg.

There is not toxicity for any doses in any samples (sample 1, sample 2 and sample 3 as defined above).

Acute oral administration of the samples as defined above did not induce acute toxicity to a maximum dose of 2000 mg/kg after 24 hours of administration, nor any signs of inducing mortality.

Figure 2:
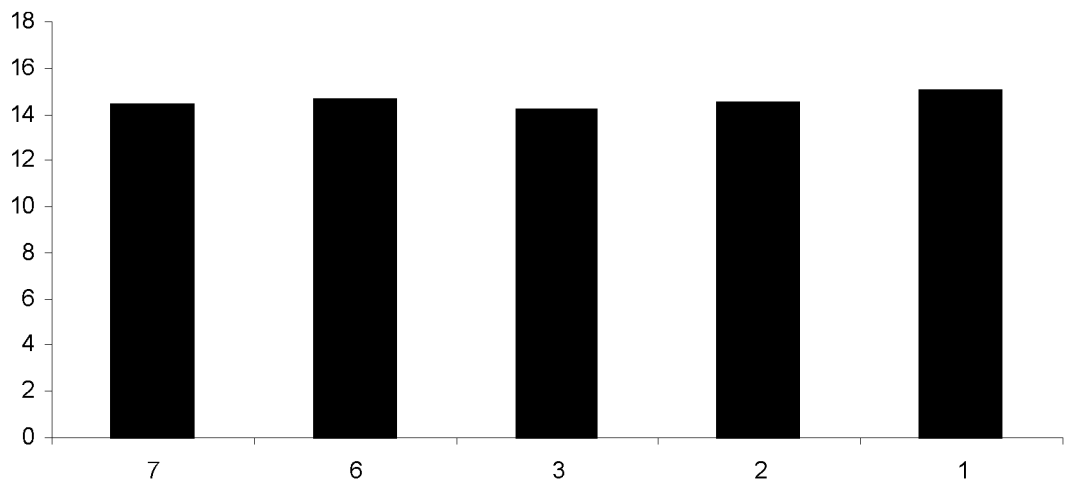
FIG. 2 shows the average amount of food (in grams) ingested by rats fed with different samples, including the sample according to the invention, yolk extract (2), and the comparative samples: embryonic extract (1), not incubated egg (3), non fertilized egg (6) and water control (7).
Figure 3:
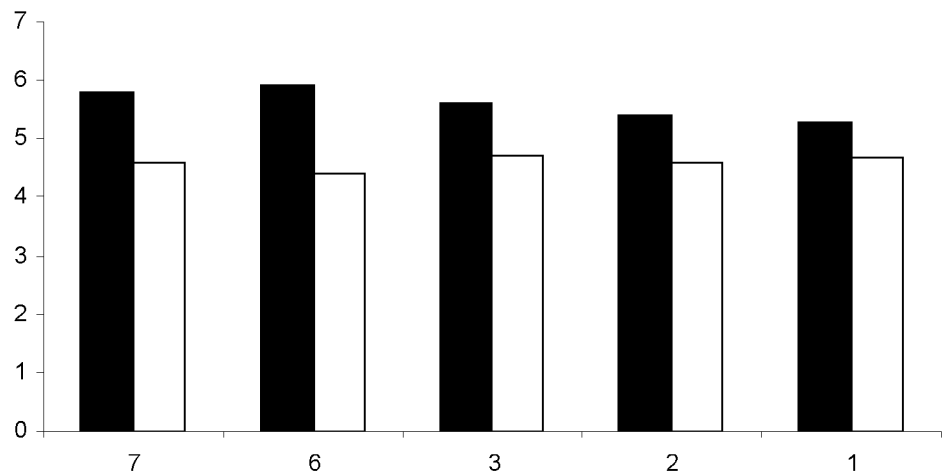
FIG. 3 shows the daily weight gain in percentage terms for male rats (black column) and for female rate (white column) fed with different samples, including the sample according to the invention, yolk extract (2), and the comparative samples: embryonic extract (1), not incubated egg (3), non fertilized egg (6) and water control (7).

Further, the ingestion and the growth animals are similar in the animals that are fed with the different samples as shown in FIG. 2. In particular, this figure shows the average amount of food (in grams) ingested by the animals. FIG. 3 shows the daily weight gain in percentage terms for male rats (black column) and for female rate (white column). This weight gain was calculated as the average of the increases with reference to the weight value of the last measuring by day and it is expressed in percentage terms. Rats were weighed at two days intervals after the sample administration.

Example 2

Effect of the Different Samples in the Cellular Model HMEC

Based on the previous results, an assay to test the insulin growth factors signaling path was carried out. The expression of the proteins pAKT and p70S6K in different samples was monitored. These samples were: comparative embryonic extract (1), yolk extract (2), comparative not incubated egg (3), comparative non fertilized egg (6), comparative enzymatic control (4), and comparative medium control (5).

The analytical technique used to detect the proteins pAKT and p70S6K was Western blot.

Figure 4:
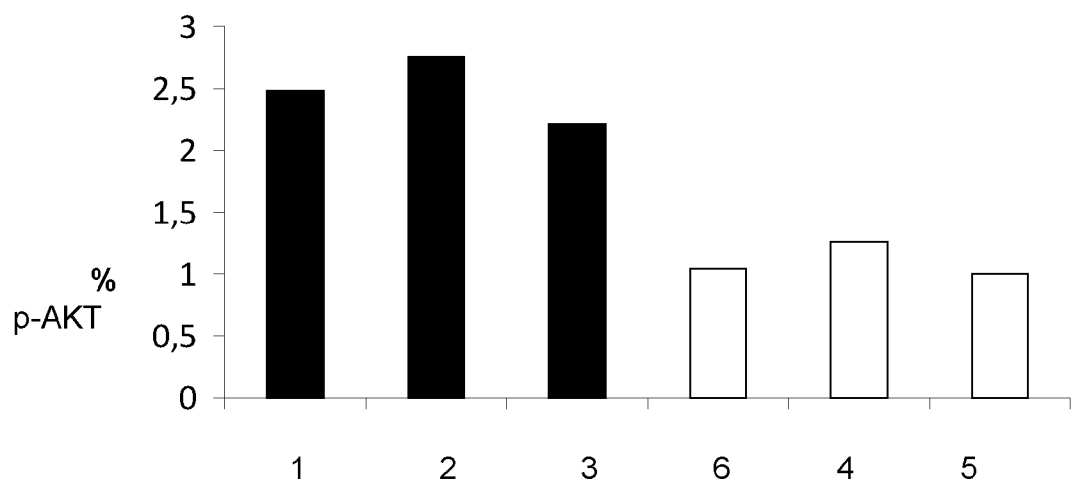
FIG. 4 shows the pAKT immunoreactivity, expressed by percentage pAKT immunoreactivity of the sample/percentage pAKT immunoreactivity of the medium control. The different samples are comparative samples: embryonic extract (1), not incubated egg (3), enzymatic control (4), medium control (5), non fertilized egg (6); and the sample according to the invention, yolk extract (2).
Figure 5:
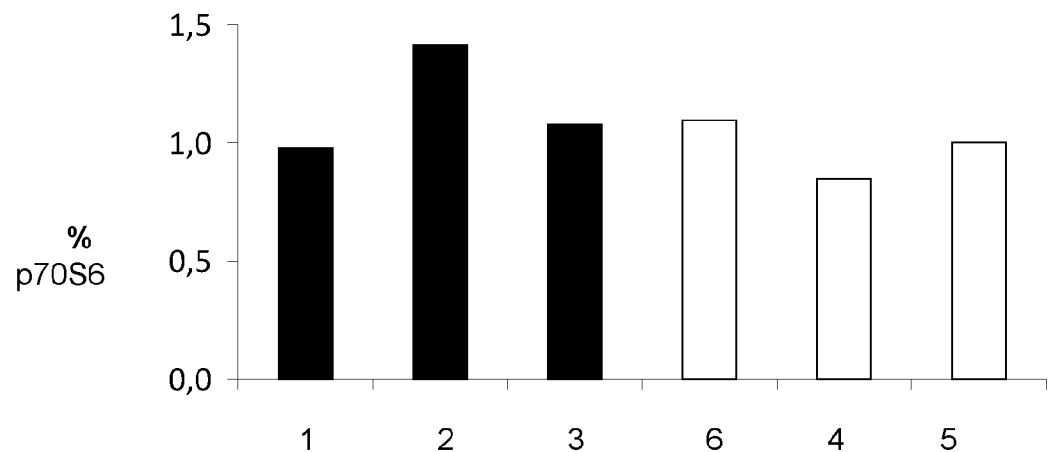
FIG. 5 shows the p70S6K immunoreactivity, expressed by percentage p70S6K immunoreactivity of the sample/percentage p70S6K immunoreactivity of the medium control. The different samples are comparative samples: embryonic extract (1), not incubated egg (3), enzymatic control (4), medium control (5), non fertilized egg (6); and the sample according to the invention, yolk extract (2).

FIG. 4 and FIG. 5 show the results. The sample 2 shows the highest activation of p70S6K and pAKT.

Example 3

Inhibition of Apoptosis

Apoptosis, or programmed cell death, is a key cellular mechanism involved in a wide variety of physiological processes.

Caspase activation assays was carried out using cell extracts. The cells were treated for 4 hour with TNFα (tumoral necrosis factor) 20 ng/mL with ciclohexamide 30 microg/mL, and with the samples 1, 2, 3, 4 and 5. The caspase 3 levels were determined.

Figure 6:
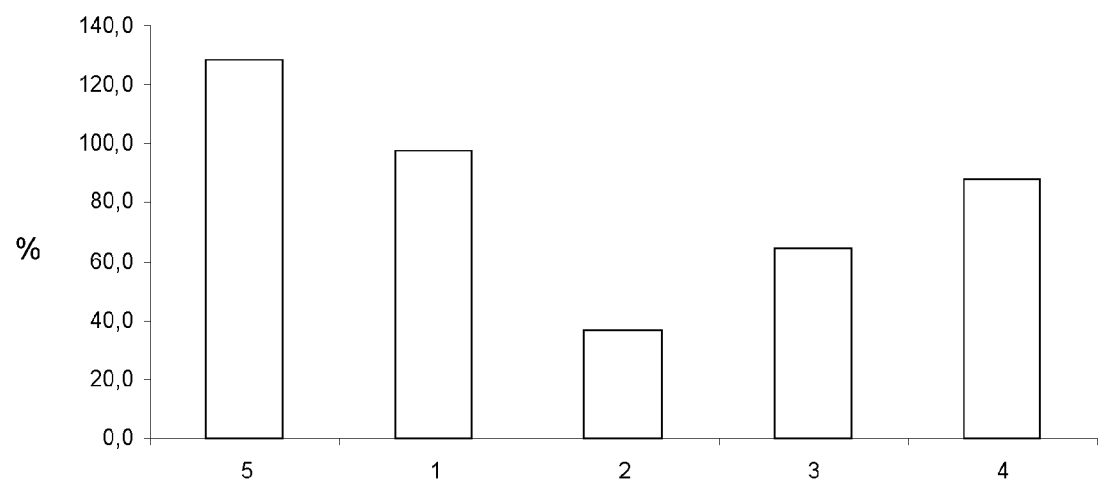
FIG. 6 shows the caspase 3 immunoreactivity, expressed by percentage caspase 3 immunoreactivity of the sample/percentage caspase 3 immunoreactivity of the medium control. The different samples are comparative samples: embryonic extract (1), not incubated egg (3), enzymatic control (4), and medium control (5), as well as for the sample according to the invention, yolk extract (2).

FIG. 6 shows the immunoreactivity of caspase 3 of the samples. The sample of the invention, sample 2 inhibited the apoptosis in a higher amount than the other samples.

Example 4-10

Clinical Uses

The examples 4-10 are regarding to the clinical use of the preparation of the invention. In the examples 4-10 the dosages were:

Dose A: 3 mL of sample 2.

Dose B: 6 mL of sample 2 or 6 mL of sample 8 (a fertilized hen egg was removed from the incubator after 24 hours. 3.6 mL of yolk and 2.4 mL of white were sucked). The sample 2 or the sample 8 were given in a random model.

The dosages were frozen stored. The dosages were thawed at room temperature ten minutes before ingestion. The ingestion was carried out one hour before meals. The administration was sublingual.

Example 4

Patient: women, 46 years old. Non toxic habits. Penicillium allergic patient.

Clinical history: tonsil stones removal, ligament hyperlaxity, bilateral patellofemoral syndrome, fibrocystic mastopathy, traffic traumatism, and herpes zoster.

Medical disorders: fibromyalgia (degree III), chronic fatigue syndrome (degree II), adaptive depressive syndrome, hypoparathyroidism, mucous dryness, and ligament hyperlaxity.

Since 2009 the fatigue increased and the patient could not work. On 22 Nov. 2010 the patient suffered low back pain, scoliosis, cervical and lumbar arthrosis, general and severe pain over last years, muscular fatigue after very little efforts, muscular contracture, insomnia, anorgasmia, motor instability. Memory and concentration patient was affected. The patient can not drive.

It was detected by analytical methods a low level of the parathyroid hormone (PTH) and a low level of the vitamin D. The thyroid-stimulating hormone was little high (3.74). Normal EMG (Electromiography). Column x ray with degenerative signs at the level of L4/15 and L5/s1 and a decrease in the height of space between vertebrae. Cervical vertebra column x ray revealed the presence of osteophytes C3/C4. Kidney and bladder ultrasound was normal. Densytometry showed osteopenia.

Treatment: Lyrica 75 (Pregabaline), Valdoxan (Agomelatine), Naprosyn (naproxen), Myolastan (tetrazepam), Alprazolam (a triazolobenzodiazepine), Duphalax (lactulose), Condrosan (Condroitin sulpahte), Hidroferol (Calcifediol), Optovte B12 (cyanocobalam in), Viscofresh (carmellose sodium) Melatonin.

The patient started the treatment with two doses B before breakfast, the second week of May 2011 during one month. Then the patient took four doses B before breakfast and lunch. During August the patient took five doses B, two before breakfast, two before lunch and one before dinner.

After four months the muscular pain and the fatigue decreased. The patient recovered the physical activity and the good mood. The patient improved the depressed mood, the concentration, the memory, the sexual life and the sleep.

These results show that the egg preparation of the invention comprises some essential nutrients that restore the lost homeostasis by the fibromyalgia and the chronic fatigue syndrome.

Example 5

Patient: women, 32 years old. Medical disorders: Psoriasis guttata and hypothyroidism, stress and depressive symptoms.

Clinical history: allergic reaction symptoms, analgesic and beta lactam antibiotic, allergic patient Treatment: antihistaminic and cortisone On June 2010, the patient started the treatment with four doses A, two before breakfast and two before lunch, during four months. Then the patient took three doses B, two before breakfast and one before lunch. Currently, the patient takes two doses B before breakfast.

After the second month the psoriasis and the allergic symptoms improved.

These results show that the damaged tissue is regenerated. The egg preparation of the invention comprises multiple growth factors at a point with high activity allowing the stimulation of a natural antigenic mechanism of the skin.

Example 6

Patient: woman, 62 years old. Medical disorders: Monoclonal gammopathy.

Clinical history: On 2001 mammal cancer. The two mammal glands were extirpated.

On May 2010, the patient started the treatment with two doses A before breakfast. Then the patient took three doses B, two before breakfast and one before lunch.

On July 2011 the monoclonal gammopathy disappeared.

Example 7

Patient: man, 55 years old. Medical disorders: multiple sclerosis since 1989. First outbreak on 1985. The first analytic showed demyelinating multifocal disorders of the central nervous system. Abnormalities of the cervical somatosensory evoked potential (SEP). Brainstem Auditory evoked potential (AEP) showed protuberances.

Clinical history: on 1989 the patient went to a neurological surgery, six years before the patient showed the sudden appearance of a fallen right foot, which deteriorated progressively to improve later without treatment. On 1985, the patient showed an episode of double vision limited in the time. Hereinafter he showed weakness in the low contra lateral extremity. In the neurological exploration, there was verified the presence of a vestibular residual syndrome, horizontal rotary nistagmus to the external right look, conjugated curvature of the left indexes. Positive Romberg. Also abolition of cutaneous abdominal reflexes and cutaneous sole indifferent reflexes. The patient showed multiple demyelinating periventricular lesions of frontal predominance and left occipital, other one in the back arm of internal left capsule and small nodular injuries in brain and trunk. Spinal injuries were not verified.

On January 2011 the patient showed multiple sclerosis, constipation, urine incontinence, the patient carries bladder permanent catheter, decubitus ulcer, movicol (macrogol) intolerance, the patient had not toxic habit, not allergy not alimentary intolerance, not mobility, the patient used wheelchair for mobility, the patient was conscious. The quality of life for 25 years of degenerative evolution of the disease had showed different conditions with repercussion in the mental condition. The verbal communication was damaged nevertheless the patient realized the effort communicating to very low level of sound, levels of anxiety being observed. The patient realized homeopathic treatment and physiotherapy once for week.

On February 2011, the patient started the treatment with five doses B, three before breakfast and two before lunch, during three month. Then, the patient took two doses A and five doses B, two doses A and two doses B before breakfast, two doses B before lunch and one dose B before dinner.

After the treatment the physiotherapist noticed that the patient developed force in the lower extremity. The patient showed voluntary movement of the toes and the fingers and the patient felt deep sensibility. After the treatment the defecation was normal and there was not flatulence.

Example 8

Patient: man, 55 years old. Medical disorders: cauda equina syndrome became for herniated disc with extremely serious bilateral axonal injury L5-S1. No signs of reinnervation appear since 2004.

Clinical history: the patient suffers from continued lower back pain. On 2004 led to paralysis of the lower body. Sciatica was diagnosed. After three days with pain herniated disc was diagnosed. The patient was undergone surgery in a clinic. After the operation the patient started the rehabilitation. The rehabilitation was extended over 4 month. After the rehabilitation the patient showed mobility in the left foot. The patient stood up. The patient experienced intense lumbar pain. The patient lost feeling and mobility in the right foot. Awkward walk.

On April 2011, the patient started the treatment with eight doses B, four before breakfast and four before dinner, during five month.

After three weeks, the patient had more energy. After four weeks the patient didn't feel lumbar pain. The patient felt the right foot and elevated the toes.

On August 2011, first signs of reinnervation in left calf muscles were found. Colateral reinnervation of the anterior left tibial muscle was increased progressively.

Example 9

Patient: woman, 20 years old. Medical disorders: Friedreich ataxia with several symptoms, for example muscle weakness in the arms and legs, the patient had walking difficulties and could not walk alone.

Clinical history: the patient got stem cell treatment

On May 2011, the patient started the treatment with one dose B before breakfast. During three months the dose was increased until six doses B, three before lunch and three before dinner.

The treatment restored patient vitality. The patient became more resistant to physical effort. The patient improved the sensibility in the foot. The patient improved the coordination of the lower extremities.

Example 10

Patient: man, 76 years old. Medical disorders: chronic obstructive pulmonary disease (COPD) grade IV, diabetes II, auricular fibrillation, lower extremities deep venous thrombosis, hypoventilation, severe acute respiratory syndrome.

Clinical history: oxygen therapy and permanent antibiotic treatment.

On 2005, the patient suffered from pulmonary emphysema. The patient has a smoking history. The patient smoked until he was 60 years all. On 2009 the patient suffered tachycardia, thoracic pain. The patient suffered paroxysmal supraventricular. Home oxygen. On 2010 the patient was treated for bilateral phlebitis with sintrom. Biphosphonate therapy. Pathologycal crush at T7. The patient suffered lethargy and bradycardia with dizziness.

On may 2011 the patient started the treatment with three doses B two before breakfast and one before lunch. One month later the dose was increased until six doses B, two before breakfast, two before lunch and two before dinner.

After the treatment the patient felt better, the treatment restored patient vitality. The patient improved the gastritis problem. The patient improved the symptoms of COPD. The recurrent respiratory crisis disappeared. It was not necessary the home oxygen. After three months from the patient started the treatment, the patient didn't need the oxygen.

Example 11

Experimental Autoimmune Encephalitis Study

Experimental Autoimmune Encephalitis (EAE) is an animal model used for studying multiple sclerosis (MS). In this model of EAE, activation of the immune system was induced by immunization with Myelin Oligodendrocyte Glycoprotein (MOG). About 10 days after immunization with MOG (onset phase), the animals began to suffer from motor disturbances that gradually increased reaching its peak after 20-21 days (peak phase). In subsequent days, the animals experienced remission until before progressing onto a chronic phase to the day 30. Some of the animals did not reach the chronic phase and died during the peak phase.

The double blind study was conducted using 6 experimental groups of female C57BL/6 mice:
  Group A: control animals without EAE induction, untreated (n=4).
  Group B: control animals without EAE induction treated with placebo (comparative sample 6, non fertilized egg (6)) (n=4).
  Group C: control animals without EAE induction treated with the egg preparation of the invention (yolk extract (2)) (n=4).
  Group D: animals with induced EAE without treatment (n=10).
  Group E: animals with induced EAE treated with placebo (comparative sample 6, non fertilized egg (6) (n=10).

Group F: animals with induced EAE treated with the egg preparation of the invention (yolk extract (2)) (n=10).

EAE induction was performed by subcutaneous immunization in the back region with an emulsion of $MOG_{35-55}$ (encephalitogenic peptide of myelin oligodendrocyte glycoprotein) in complete Freund's adjuvant containing inactivated mycobacterium tuberculosis. Furthermore, the mice received a pertussis toxin administration immediately and 48 hours after immunization. The different treatments were administered daily at the same time for 43 days from the day of immunization until the day of slaughter. Oral administration was used. The animals were given access to the treatment for two hours in an isolated cage. In the event that the animal had not taken the entire dose, this was administered using a syringe. The dose administered was 0.5 mL per animal per day. During the study animals were kept under controlled temperature and humidity conditions and had ad libitum access to water and food.

Weight and clinical symptoms of animals were recorded daily. Clinical symptoms were evaluated using the following clinical score test: 0: no clinical symptoms; 0.5: partial loss of tail tone; 1: paralysis of the tail; 2: paraparesis of hindlimb; 3: complete paralysis of hindlimb; 4: tetraparesis; and 5: tetraplegia.

Results

1) The effects of the administration of the egg preparation of the invention (yolk extract (2)) to control animals without EAE induction (Group C) were comparable to those observed in control groups A and B, with no changes in weight and clinical symptoms.

2) The administration of the egg preparation of the invention (yolk extract (2)) to animals with induced EAE (Group F) showed beneficial effects in comparison with groups D and E. In particular, weight loss was avoided in part in animals of Group F.

Figure 7A:
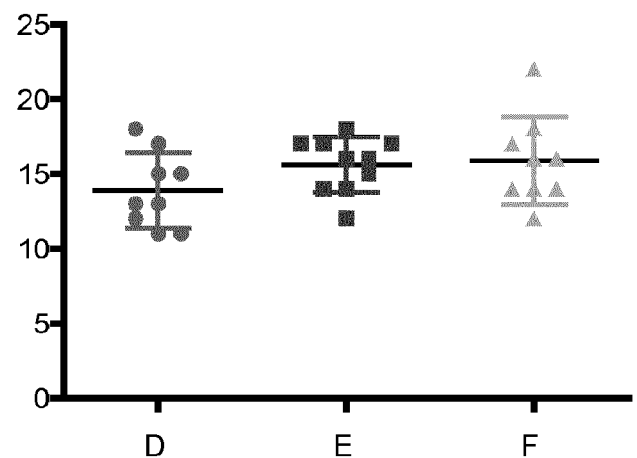
FIG. 7A shows the day of onset of clinical symptoms.
Figure 7B:
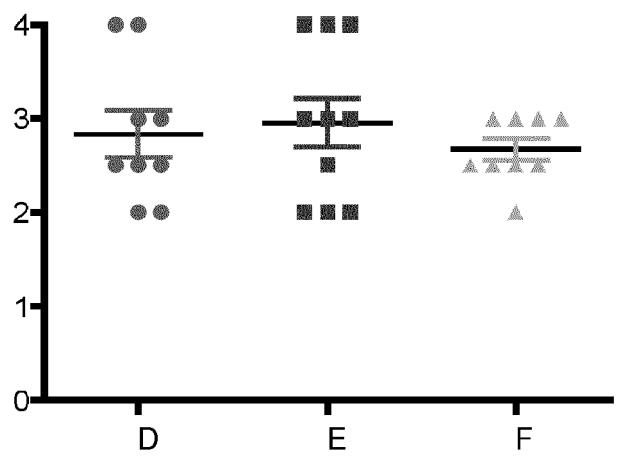
FIG. 7B shows the highest clinical score in the peak phase.
Figure 7C:
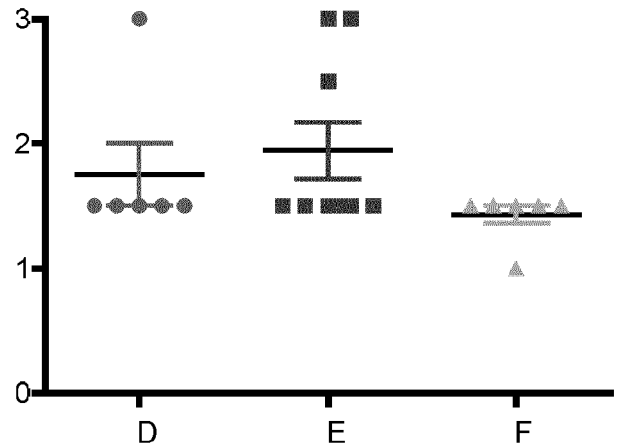
FIG. 7C shows the lowest clinical score in the chronic phase.

3) The administration of the egg preparation of the invention (yolk extract (2)) to animals with induced EAE (Group F) also induced major changes in the clinical course of EAE with respect to groups D and E. Thus, animals of Group F showed a lower overall severity in the clinical course of the disease (FIG. 7). Differences were observed during the onset phase, where animals of Group F showed a delay on the day of the onset of symptoms with respect to animals of groups D and E (FIG. 7A). The highest clinical score values in the peak phase for animals of Group F (around 3) were lower than the one of the animals of groups D and E (in some cases even tetraparesis, score 4, was reached) (FIG. 7B). During the chronic phase, animals of Group F became chronic with lower clinical score values, around 1.5. In contrast, animals in the group D showed more variability, reaching different degrees of clinical involvement (FIG. 7C).

4) Finally, a significant reduction in mortality was observed in the animals of Group F in comparison to animals of Group D. In particular, 20% of the animals of the Group F died, while 45% of the animals of Group D died.

Neuronal Regeneration Model

Axotomy is a neuronal injury model used for studying neuronal regeneration. In this model the right facial nerve was transected (axotomy) at the level of the foramen. The axotomy lead to Wallerian degeneration of all sectioned axons and to retrograde degeneration in an important number of motor neurons located in the ipsilateral brainstem facial nucleus. It is known that only those neurons of the facial nucleus which are able to regenerate their axons are able to survive. The unlesioned contralateral facial nucleus can be used as control.

The study was conducted using 5 experimental groups of C57BL16 mice:

Group A: control animals not subjected to axotomy, untreated.

Group B: control animals not subjected to axotomy treated with placebo (comparative sample 6, non fertilized egg (6)) (n=4).

Group C: control animals not subjected to axotomy treated with the egg preparation of the invention (yolk extract (2)) (n=4).

Group D: axotomized animals treated with placebo (comparative sample 6, non fertilized egg (6)) (n=8).

Group E: axotomized animals treated with the egg preparation of the invention (yolk extract (2)) (n=10).

The different treatments were administered daily at the same time from the day of axotomy until the day of slaughter. The dose administered was 0.5 mL per animal per day. The animals were given access to the treatment for two hours in an isolated cage. In the event that the animal had not taken the entire dose, this was administered using a syringe. During the study animals were kept under controlled temperature and humidity conditions and had ad libitum access to water and food.

Analysis of axonal regeneration was carried out by quantification of retrogradely labeled motor neurons in the facial nucleus with Fluorogold. This retrograde marker was injected subcutaneously at the level of vibrissae on both sides (ipsilateral and contralateral) on the 35th day after axotomy. At this time, surviving neurons were able to regenerate the axons back to their target tissues.

Regenerated axons of neurons in the facial nucleus that reached the site where the Fluorogold was injected, incorporated and retrogradely transported it into neuronal soma, which emitted intense fluorescence at the appropriate wavelength (385 nm).

After 7 additional days of survival, i.e. 42 days after axotomy, animals of different groups were anesthetized, sacrificed by cardiac perfusion with 4% paraformaldehyde in 0.1 M phosphate buffer pH 7.4 and conveniently processed for histological examination. To this end, each of the brains after being preserved in 30% sucrose and frozen in isopentane was sectioned using a cryostat, and all cuts obtained, with a thickness of 30 microns, were collected on gelatinized glass slides. Photographs of all sections containing the ipsilateral and contralateral facial nucleus of each animal were taken with an epifluorescence microscope for subsequent quantification. Fluorescent neuronal profiles (marked with Fluorogold) were counted on the photographs obtained and subsequently the Abercrombie correction was applied to evaluate stereologically the actual number of labeled neurons in each facial nucleus. The data obtained were statistically analyzed by ANOVA and T Student test.

Results

Figure 8A:
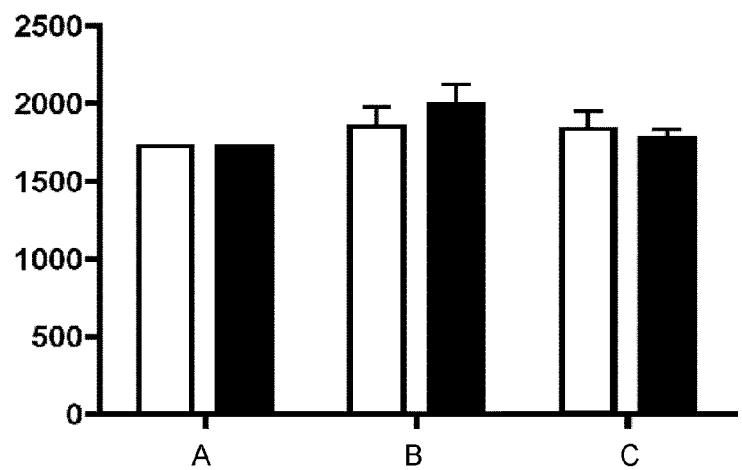
FIG. 8A shows the quantification of Fluorogold positive neurons of animals of groups A, B, and C; white column: left side, and black column: right side.

1) No significant differences were observed in the number of neurons labeled with Fluorogold in treated animals not subjected to axotomy (Groups B and C) (FIG. 8A). This indicates that the treatment with the egg preparation of the invention (Group C) within 42 days of continuous administration is safe and does not produce any type of neurodegeneration in the facial nucleus object of this study.

Figure 8B:
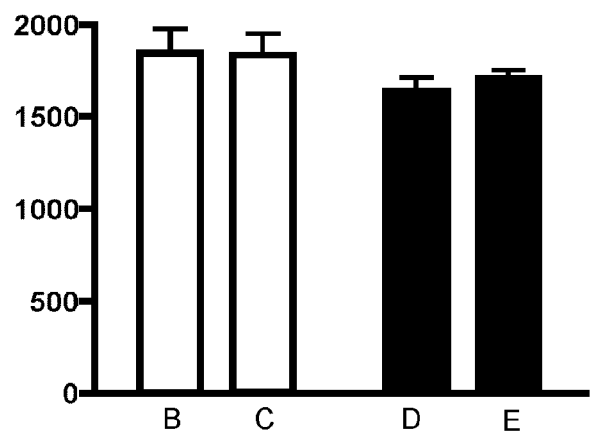
FIG. 8B shows the quantification of Fluorogold positive neurons of animals not subjected to axotomy (Groups B, and C), and of the unlesioned contralateral side in axotomized animals (Groups D and E).

2) The number of neurons labeled with Fluorogold in treated axotomized animals (Groups D and E) and in treated animals not subjected to axotomy (Groups B and C) was similar (FIG. 8B). This validated the contralateral side of groups D and E as controls in the quantitative study.

Figure 8C:
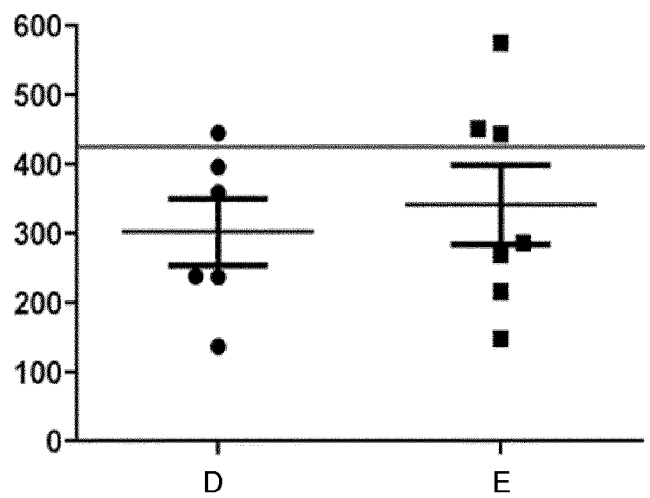
FIG. 8C shows the quantification of Fluorogold positive neurons of the ipsilateral side in axotomized animals (Groups D and E). The horizontal line above 400 indicates the unusual regeneration degree.

3) In groups D and E, the facial nerve axotomy induced degeneration of a significant percentage of neurons in the facial nucleus (FIG. 8C) which resulted in fewer neurons labeled with Fluorogold when comparing the ipsilateral to the contralateral side. However, treatment with the egg preparation of the invention (sample 2) (Group E) exerted a beneficial effect in a significant proportion of the population of axotomized animals. This was shown by a higher unusual degree of regeneration, referred to as the degree of axonal regeneration which is higher than 50% of an expected average value of regeneration. In FIG. 8C the horizontal line above 400 indicates the unusual regeneration degree. Approximately 38% of animals of Group E and only 14% of animals of Group D showed an unusually high number of neurons labeled with Fluorogold.

REFERENCES CITED IN THE APPLICATION

L. Coussens et al. in "Inflammation and cancer", *Nature* 2002, vol. 420, pp. 860-867
EP0904090
CA2197050
WO0191777
WO2009115429

The invention claimed is:

1. An egg preparation comprising a homogenous mixture of the yolk and the white extracted from a fertilized egg incubated for a period comprised between 18 hours and 36 hours, wherein the mixture of the yolk and white is in a ratio in which the amount of the white is comprised in one or more of between 2% and 40%, or between 5% and 30%, or at 10% by volume of the yolk volume;
   the homogenous mixture being obtainable by a preparation process comprising the following:
   (a) Incubating a fertilized egg for a period comprised between 18 hours and 36 hours;
   (b) Collecting an amount of the yolk and an amount of the white of the incubated fertilized egg obtained in the previous part (a), and mixing the yolk and the white in a ratio in which the amount of the white is comprised in one or more of between 2% and 40%, or between 5% and 30%, or at 10% by volume of the yolk volume;
   (c) Homogenizing the mixture of yolk and white obtained in part (b); and
   (d) Quenching the egg preparation obtained in part (c).

2. The egg preparation according to claim 1, wherein the white is internal fluid white.

3. The egg preparation according to claim 2, further comprising one or both of external fluid white and dense white, in an amount such that the sum of internal fluid white, external fluid white, and dense white in the egg preparation is up to 99% by volume of the sum of yolk and total white volumes.

4. A process for preparing the egg preparation as defined in claim 1, which comprises:
   (a) Incubating a fertilized egg for a period comprised between 18 hours and 36 hours;
   (b) Collecting an amount of the yolk and an amount of the white of the incubated fertilized egg obtained in the previous step, and mixing the yolk and the white in a ratio in which the amount of the white is comprised between 2% and 40% by volume of the yolk volume;
   (c) Homogenizing the mixture of yolk and white obtained in step b); and
   (d) Quenching the egg preparation obtained in step c).

5. The process according to claim 4, further comprising an additional step of refrigerating the incubated egg obtained in step a).

6. The process according to claim 4, wherein the quenching step comprises a freezing step or a freeze drying step.

7. A functional food comprising an egg preparation as defined in claim 1.

8. A dietary supplement comprising an egg preparation as defined in claim 1.

9. A pharmaceutical composition comprising an effective amount of an egg preparation as defined in claim 1, together with one or more pharmaceutical excipients or carriers.

10. A veterinary composition comprising an effective amount of an egg preparation as defined in claim 1, together with one or more veterinary excipients or carriers.

11. A cosmetic composition comprising an effective amount of an egg preparation as defined in claim 1, together with one or more cosmetic excipients or carriers.

12. A method of treatment of a mammal, including a human, suffering from acute or chronic pain, said method comprising administering to said mammal, including a human, a therapeutically effective amount of the egg preparation as defined in claim 1 together with acceptable excipients of carriers.

13. A method of treatment according to claim 12, wherein the pain is fibromyalgia.

14. A method of treatment of a mammal, including a human, suffering from a degenerative condition, said method comprising administering to said mammal, including a human, a therapeutically effective amount of the egg preparation as defined in claim 1 together with acceptable excipients or carriers.

15. A method and treatment according to claim 14, wherein the condition is selected from the group consisting of psoriasis, multiple sclerosis, and Friedreich ataxia.

16. A method of treatment of a mammal, including a human, suffering from an inflammatory condition, said method comprising administering to said mammal, including a human, a therapeutically effective amount of the egg preparation as defined in claim 1, together with acceptable excipients or carriers.

17. A method and treatment according to claim 16, wherein the condition is cancer.

18. A cosmetic method for skin care of a mammal, including a human, said method comprising administering to said mammal, including a human, an effective amount of an egg preparation as defined in claim 1, together with acceptable excipients or carriers.

19. A cosmetic method for hair or fur care of a mammal, including a human, said method comprising administering to said mammal, including a human, an effective amount of an egg preparation as defined in claim 1 together with acceptable excipients or carriers.

* * * * *